(12) United States Patent
Lo

(10) Patent No.: US 9,532,776 B2
(45) Date of Patent: Jan. 3, 2017

(54) SUTURE ANCHOR AND ASSOCIATED SYSTEMS AND METHODS

(71) Applicant: Ian Lo, Calgary (CA)

(72) Inventor: Ian Lo, Calgary (CA)

(73) Assignee: Soteria Industries, Inc., Calgary, Alberta, CA (US)

( * ) Notice: Subject to any disclaimer, the term of this patent is extended or adjusted under 35 U.S.C. 154(b) by 392 days.

(21) Appl. No.: 13/922,733

(22) Filed: Jun. 20, 2013

(65) Prior Publication Data

US 2014/0379028 A1    Dec. 25, 2014

(51) Int. Cl.
*A61B 17/04* (2006.01)

(52) U.S. Cl.
CPC ....... *A61B 17/0401* (2013.01); *A61B 17/0469* (2013.01); *A61B 2017/044* (2013.01); *A61B 2017/0409* (2013.01); *A61B 2017/0445* (2013.01); *A61B 2017/0448* (2013.01); *A61B 2017/0453* (2013.01); *A61B 2017/0458* (2013.01)

(58) Field of Classification Search
CPC .................. A61B 17/0401; A61B 2017/0409; A61B 2017/0446; A61B 17/04
See application file for complete search history.

(56) References Cited

U.S. PATENT DOCUMENTS

| 2010/0016869 A1* | 1/2010 | Paulk | A61B 17/0401 606/144 |
| 2010/0292732 A1* | 11/2010 | Hirotsuka | A61B 17/0401 606/232 |

* cited by examiner

*Primary Examiner* — Victor Nguyen
(74) *Attorney, Agent, or Firm* — Bryan D. Zerhusen; Locke Lord LLP

(57) ABSTRACT

Exemplary embodiments of a suture anchor are provided that generally include a suture anchor body including a securing structure for securing the suture anchor in tissue or bone. The suture anchor body includes an internal cavity configured and dimensioned to receive therein a suture and a locking pin. Exemplary embodiments are also directed to suture anchor systems that generally include a suture anchor and a driver configured and dimensioned to interlock relative to the suture anchor. Exemplary embodiments are further directed to methods of anchoring a suture in tissue or bone that generally include providing a suture anchor, passing the suture through the suture anchor body, and driving the suture anchor into the tissue or bone.

6 Claims, 10 Drawing Sheets

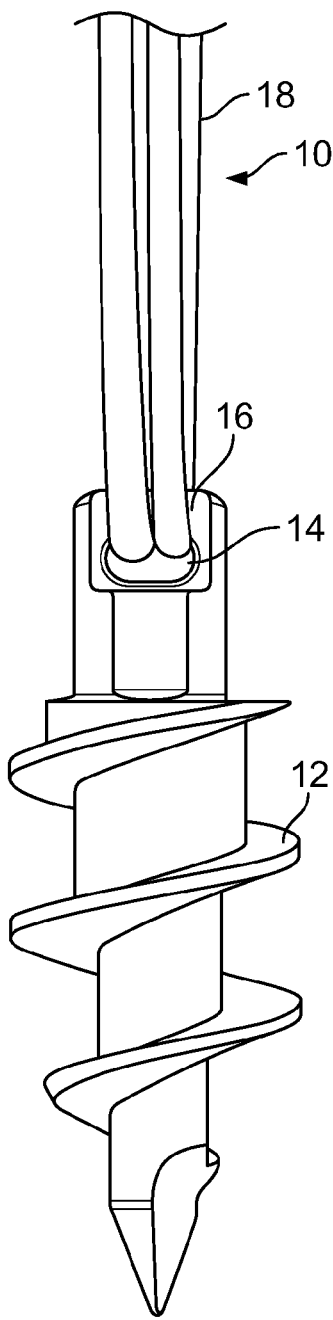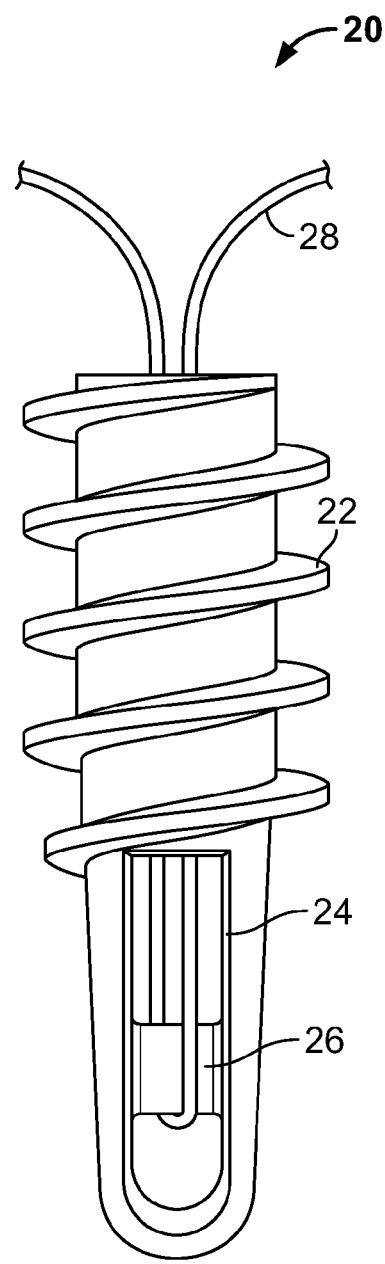
FIG. 1A
(Prior Art)
FIG. 1B
(Prior Art)

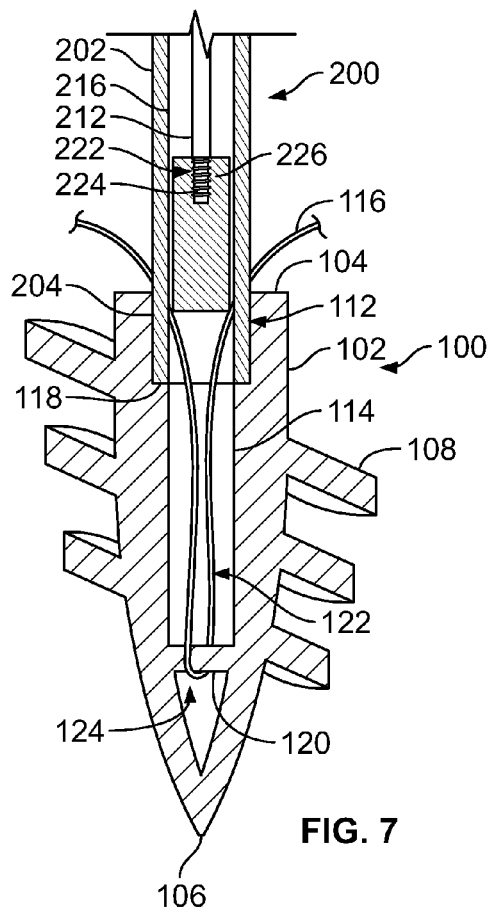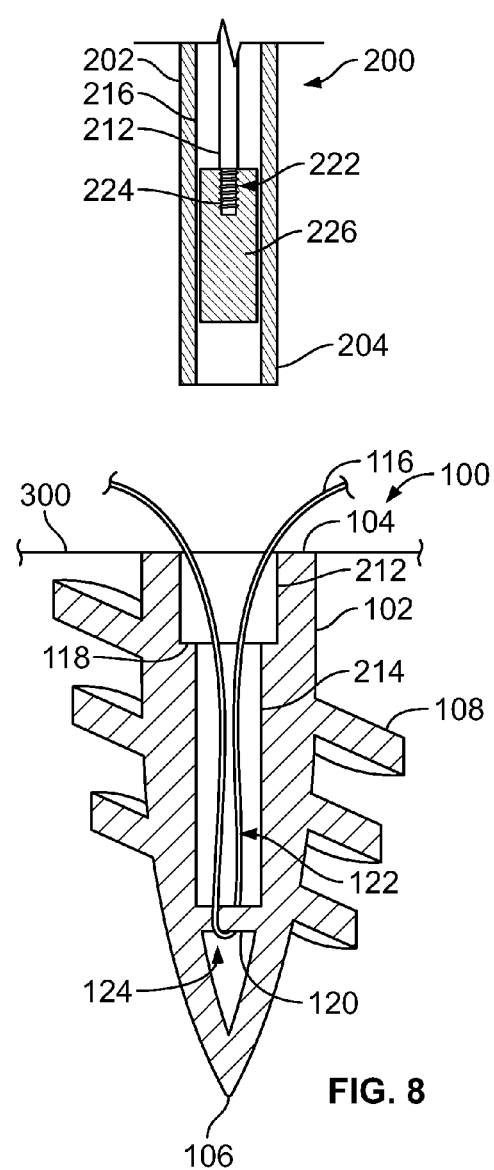
FIG. 7
FIG. 8

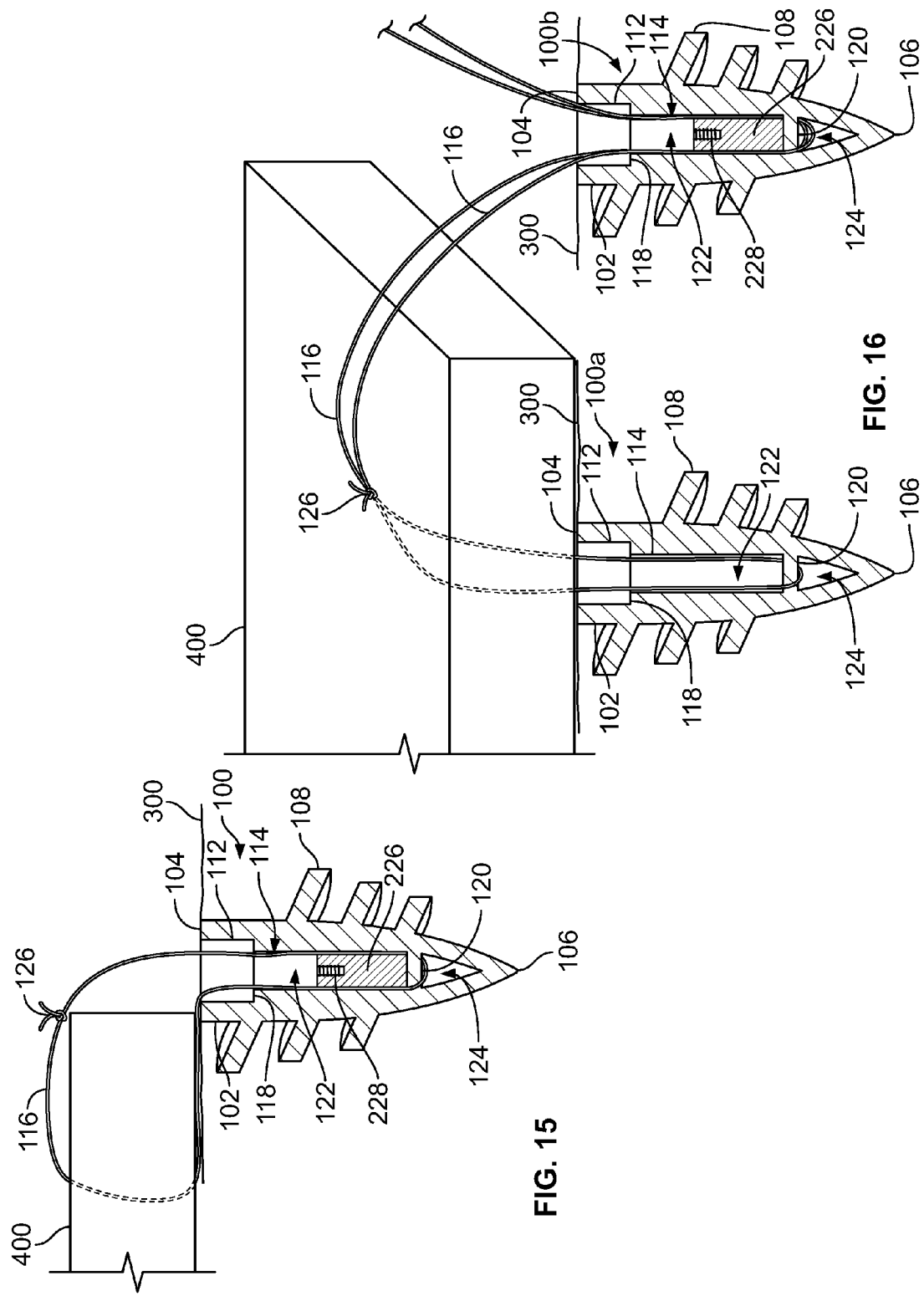

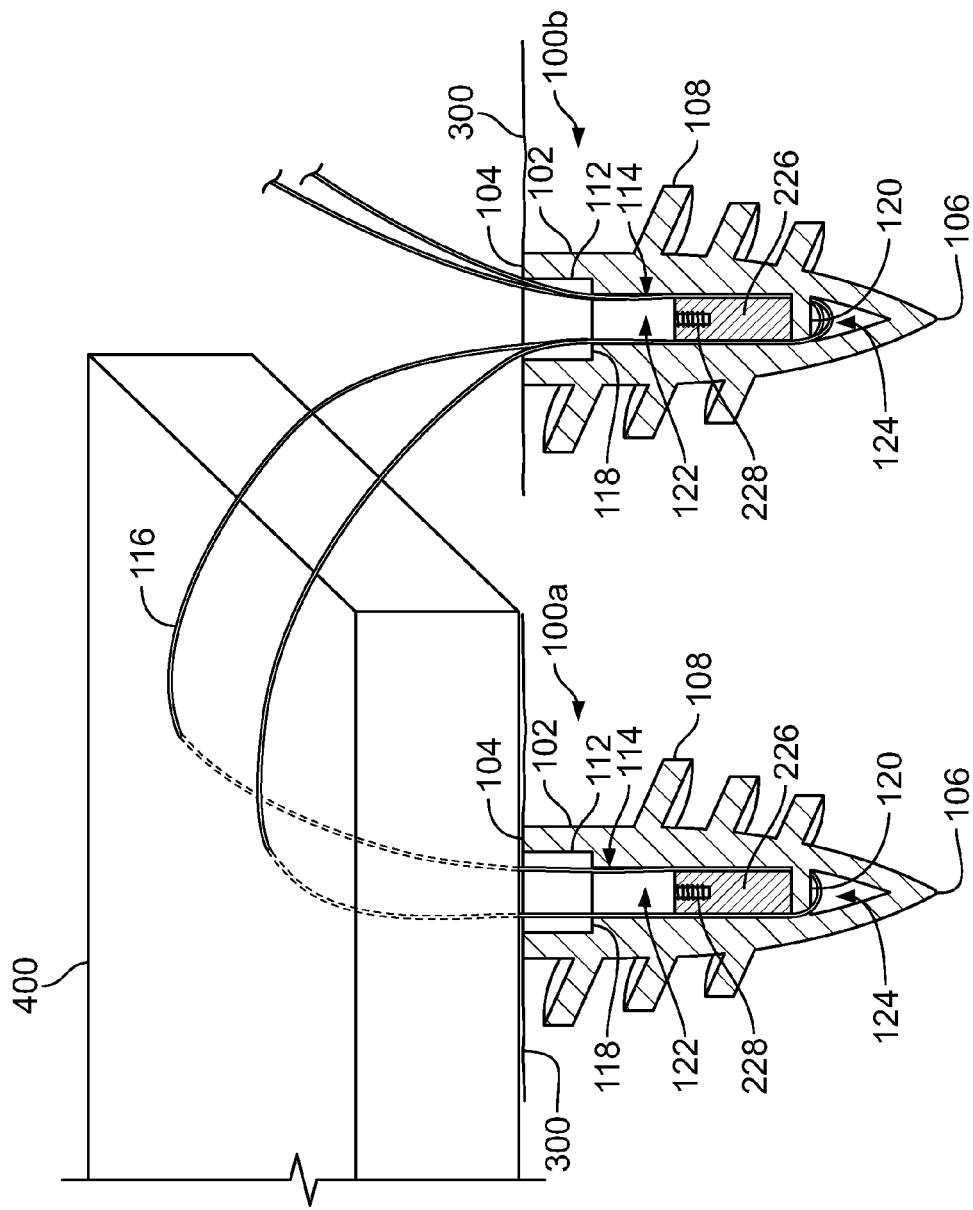

SUTURE ANCHOR AND ASSOCIATED SYSTEMS AND METHODS

TECHNICAL FIELD

The present disclosure relates to a suture anchor and, more particularly, to a suture anchor with a sliding, a non-sliding and a knotless suturing capability.

BACKGROUND

Suture anchors are common implants used in the medical industry for soft tissue fixation to bone. These implants are commonly used in orthopedic applications, such as during tendon fixation or ligament fixation to bone. Suture anchors in the industry generally include an anchor body which is loaded with one or more sutures. The suture anchor can be inserted into and secured in the bone by, e.g., threads (i.e., a corkscrew design), a ribbed design (i.e., an interference screw design), a winged design (i.e., a harpoon shaped anchor), and the like. Once the suture anchor has been secured in the bone, one or more sutures can be passed through the soft tissue, such as a tendon or a bone, and a knot can be tied to reduce and secure the tendon to the bone. Some suture anchors may be preloaded with one or more sutures before the suture anchor is to be secured in the bone. For example, a suture anchor may be preloaded with single or multiple sutures, e.g., one to three sutures.

With reference to FIGS. 1A and 1B, alternative designs of a sliding suture anchor known in the industry are provided. FIG. 1A shows a suture anchor 10 which includes threads 12 on an outer surface and an eyelet 14 formed with a post 16 at a proximal end of the suture anchor 10. One or more sutures 18 can be passed around the internal eyelet 14 or post 16 and the threads 12 of the suture anchor 10 can be driven into bone, while permitting the sutures 18 to slide through or around the eyelet 14 and post 16. Similarly, FIG. 1B shows a suture anchor 20 which includes threads 22 on an outer surface and an eyelet 14 formed below the threads 22 with a post 26. One or more sutures 28 can be passed through the body of the suture anchor 20 and around the internal eyelet 24 or post 26 and the threads 22 of the suture anchor 20 can be driven into bone, while permitting the sutures 28 to slide around the internal post 26 and through the body of the suture anchor 20. The sliding suture anchor 10, 20 may be used when tying knots in the suture 18, 28 or can allow sliding knots to be utilized when tying the knot during soft tissue fixation to bone.

With reference to FIG. 1C, a non-sliding suture anchor 30 is shown. The suture anchor 30 can include threads 32 on an outer surface and a distal eyelet 34 external to the bulk of the suture anchor 30 body. One or more sutures 36 can be passed through the eyelet 34 and, as the suture anchor 30 is secured into a bone with the threads 32, the suture 36 can be locked between the suture anchor 30 body and/or threads 32 and the bone by interference and frictional forces which prevent the suture 36 from sliding. Since the suture 36 cannot slide through the suture anchor 30, the suture 36 can be tied using a non-sliding knot. In knotless applications, rather than tying a non-sliding knot, the suture 36 can be held in place only by the frictional forces generated by the suture anchor 30 against the bone.

However, the suture anchors illustrated in FIGS. 1A-1C do not provide the option of inserting an anchor preloaded with one or more sutures into tissue or bone for a sliding suture, a non-sliding suture and a knotless suture technique. For example, the suture anchors 10, 20 of FIGS. 1A and 1B can only be used for sliding suture applications, while the suture anchor 30 of FIG. 1C can only be used for non-sliding suture applications. As such, different types of suture anchors 10, 20, 30 and associated drivers may be required by a surgeon during a single surgical procedure, thereby complicating the surgical procedure.

Thus, a need exists for suture anchors which provide a sliding suture, a non-sliding suture and a knotless suture capability. These and other needs are addressed by the suture anchors and associated systems and methods of the present disclosure.

SUMMARY

In accordance with embodiments of the present disclosure, exemplary suture anchors are provided that include a suture anchor body including a securing structure, e.g., threads, an interference fit structure, a retractable harpoon, and the like, for securing the suture anchor in tissue or bone. The suture anchor body includes an internal cavity, i.e., a second cavity, configured and dimensioned to receive therein a suture and a locking pin. The exemplary suture anchor can be adapted for sliding, non-sliding and knotless suturing techniques.

The suture anchor body includes an additional internal cavity, i.e., a first cavity, located adjacent to the internal cavity configured and dimensioned to interlock with a driver for driving the suture anchor into the tissue or bone. The internal cavity includes an internal post forming an eyelet in the internal cavity. The eyelet can be configured and dimensioned to slidably receive the suture therethrough. The suture anchor body can be fabricated from a group consisting of a metal, a bioabsorbable material, a biocomposite material, a polyether ether ketone, and the like.

In accordance with embodiments of the present disclosure, exemplary suture anchor systems are provided that include a suture anchor and a driver. The suture anchor includes a suture anchor body including a securing structure for securing the suture anchor in tissue or bone. The suture anchor body includes an internal cavity configured and dimensioned to receive therein a suture and a locking pin. The driver can be configured and dimensioned to interlock relative to the suture anchor.

The driver can include a driver handle and a shaft. The suture anchor body includes an additional internal cavity to receive a distal end of the shaft. The driver handle includes a post for wrapping the suture thereon to lock or fixate the driver relative to the suture anchor. The driver includes a locking pin driver detachably secured to the locking pin with locking means, e.g., threads, and the like. The locking pin driver and the locking pin can be axially translatable relative to the driver handle and the shaft when the driver has been fixated relative to the suture anchor. The internal cavity of the suture anchor can include an internal post forming an eyelet in the internal cavity. The eyelet can be configured and dimensioned to receive the suture therethrough. Advancement of the locking pin into the internal cavity fixedly secures the suture within the internal cavity.

In accordance with embodiments of the present disclosure, exemplary methods of anchoring a suture in tissue or bone are provided that include providing a suture anchor. The suture anchor includes a suture anchor body including a securing structure for securing the suture anchor in the tissue or bone. The suture anchor body includes an internal cavity configured and dimensioned to receive therein the suture and a locking pin. The methods include passing the suture through the suture anchor body and driving the suture anchor into the tissue or bone.

The methods include interlocking the suture anchor with a driver for driving the suture anchor into the tissue or bone. The methods further include wrapping the suture around a post protruding from a driver handle. For a sliding suture application, the methods include disengaging the driver from the suture anchor and slidably translating the suture through the suture anchor body. For a non-sliding suture application, the methods include advancing the locking pin into the internal cavity with a locking pin driver and fixating the suture against the internal walls of the internal cavity of the suture anchor. The methods further include disengaging the locking pin driver from the locking pin.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

To assist those of skill in the art in making and using the disclosed suture anchors and associated methods, reference is made to the accompanying figures, wherein:

FIGS. 1A-1C are side and perspective views of traditional suture anchors of the prior art;

FIG. 7 is a side, cross-sectional view of an exemplary suture anchor and driver including a retracted locking pin according to the present disclosure;

FIG. 8 is a side, cross-sectional view of an exemplary suture anchor and driver according to the present disclosure;

FIG. 15 is a side view of an exemplary suture anchor securing a suture in tissue according to the present disclosure;

FIG. 16 is a side view of two exemplary suture anchors securing a suture in tissue according to the present disclosure; and FIG. 17 is a side view of two exemplary suture anchors securing a suture in tissue according to the present disclosure.

DESCRIPTION OF EXEMPLARY EMBODIMENTS

Figure 1C:
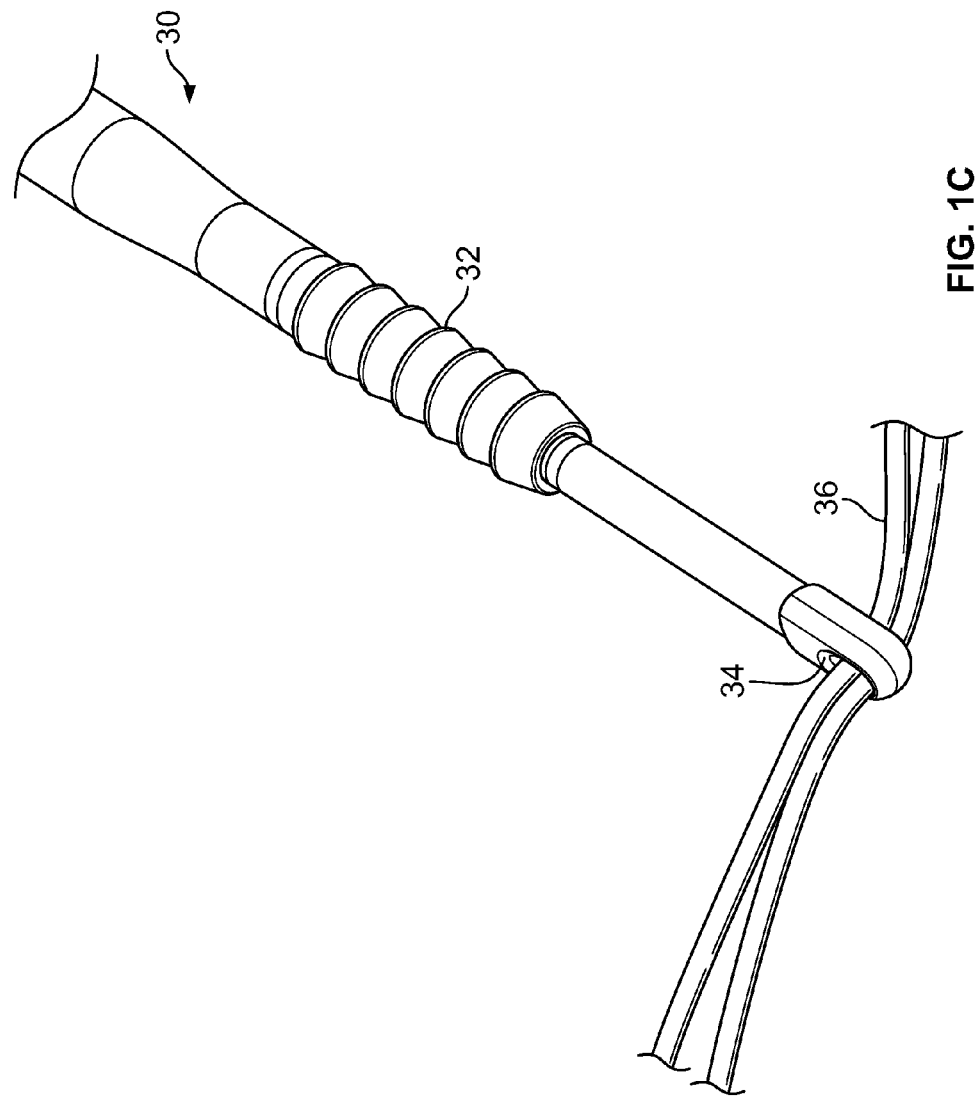
Figure 2:
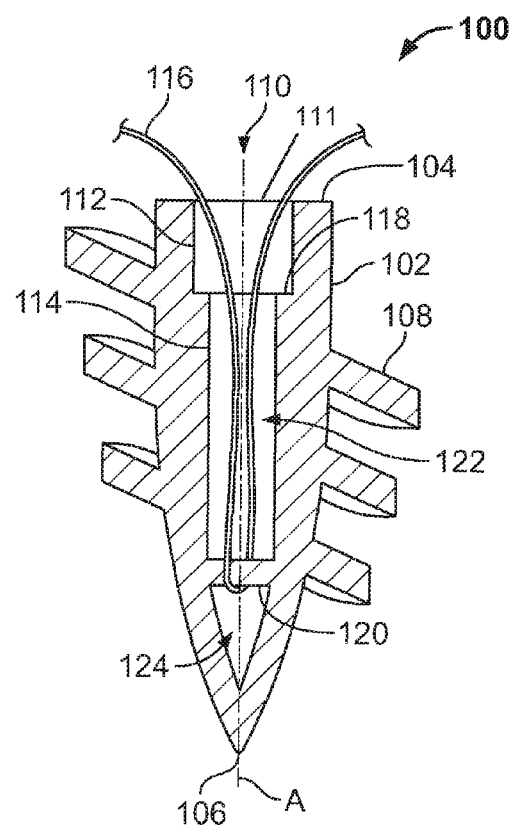
FIG. 2 is a side, cross-sectional view of an exemplary suture anchor according to the present disclosure.

Turning to FIG. 2, an exemplary suture anchor 100 is provided which advantageously allows sliding, non-sliding and knotless suture applications in a single suture anchor 100 design. The suture anchor 100 can be fabricated from materials generally used in orthopedic applications, including metal, bioabsorbable material, biocomposite material, polyether ether ketone (PEEK), and the like. The suture anchor 100 includes an anchor body 102 defining a proximal end 104 and a distal end 106. The suture anchor 100 includes a securing structure 108 positioned near or on an outside surface of the anchor body 102. The securing structure 108 can be used to secure the suture anchor 100 within tissue and/or bone. Although illustrated as threads (i.e., a corkscrew design), in some embodiments, the securing structure 108 can be, e.g., an interference fit, an expandable harpoon design, or any other methods of fixation. For example, in an expandable harpoon design (not shown), the anchor body 102 can be covered with an inserter which can be pulled off to eject the spring-loaded harpoons from the sides of the anchor body 102. Thus, the inserter can maintain the harpoons in a retracted position until fixation of the suture anchor 100 is desired. In some expandable harpoon embodiments, a pin can be actuated, e.g., pushed, to eject the spring-loaded harpoons from the sides of the anchor body 102. The proximal end 104 can define a substantially flat plane, while the distal end 106 can define a tapered point configured to be driven into tissue and/or bone.

The suture anchor 100 includes an internal cavity 110 which defines a first cavity 112 and a second cavity 114. The internal cavity 110 can open to the proximal end 104 of the suture anchor 100 at opening 111 and can extend in the direction of the distal end 106. The first cavity 112 can be configured and dimensioned to interlock relative to a driver for driving and securing the suture anchor 100 into tissue and/or bone. It should be understood that the suture anchor 100 can be driven into tissue and/or bone by initially driving the distal end 106 of the suture anchor 100 into the tissue and/or bone and, for example, rotating the suture anchor 100 to drive the securing structure 108 into the tissue and/or bone.

The second cavity 114 can be configured and dimensioned to receive therein one or more sutures 116 and, optionally, a locking pin (not shown) for non-sliding suture 116 applications. The diameter of the first cavity 112 can be dimensioned greater than the diameter of the second cavity 114, forming an edge 118 between the first cavity 112 and the second cavity 114. As will be discussed below, a distal end of the driver can be inserted into the first cavity 112 for driving the suture anchor 100 into tissue and/or bone and can further be used to insert a locking pin into the second cavity 114. The depth of the first cavity 112 can be selected to provide sufficient support for a driver inserted into the first cavity 112 to provide torque when driving the suture anchor 100 into tissue and/or bone.

The suture anchor 100 includes an internal post 120 positioned within the second cavity 114 substantially perpendicular to the vertical axis A. The internal post 122 can divide the second cavity 114 into a top portion 122 and a bottom portion 124, i.e., an eyelet. The top portion 122 can be configured and dimensioned to receive the locking pin therein, while the bottom portion 124 can permit the passage of one or more sutures 116 through the bottom portion 124 and around the internal post 120. The suture 116 can thereby slide freely around the internal post 120 to regulate a position or tension of the suture 116. Although illustrated as adjacent to the distal end 106 of the suture anchor 100, it should be understood that the internal post 120 can be positioned at any point within the second cavity 114 such that the locking pin can be inserted into and sufficiently maintained within the top portion 122.

Figure 3A:
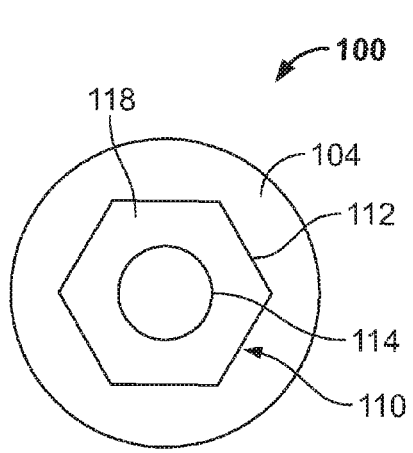
FIGS. 3A and 3B are top views of an exemplary suture anchor according to the present disclosure.
Figure 3B:
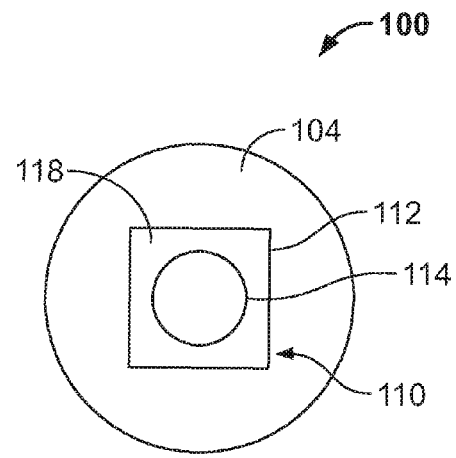

With reference to FIGS. 3A and 3B, top views of the proximal end 104 of the suture anchor 100 and the internal cavity 110 are provided. In some embodiments, the first cavity 112 can be configured for a hexagonal driver (FIG. 3A) or a square driver (FIG. 3B). In some embodiments, the first cavity 112 can be configured for alternative drivers, e.g., slotted drivers, fluted drivers, and the like, so long as the first cavity 112 remains complementary to the configuration of an interlocking driver or driver handle. In addition, although the second cavity 114 is illustrated as circular, in some embodiments, the second cavity 114 can be configured as, e.g., square, rectangular, triangular, and the like, so long as the configuration of the second cavity 114 remains complementary to the configuration of the locking pin.

Figure 4:
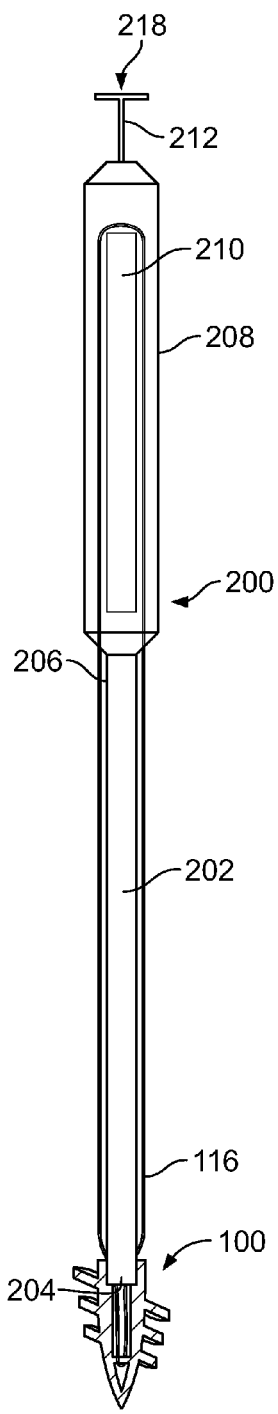
FIG. 4 is a side view of an exemplary suture anchor and driver according to the present disclosure.
Figure 5:
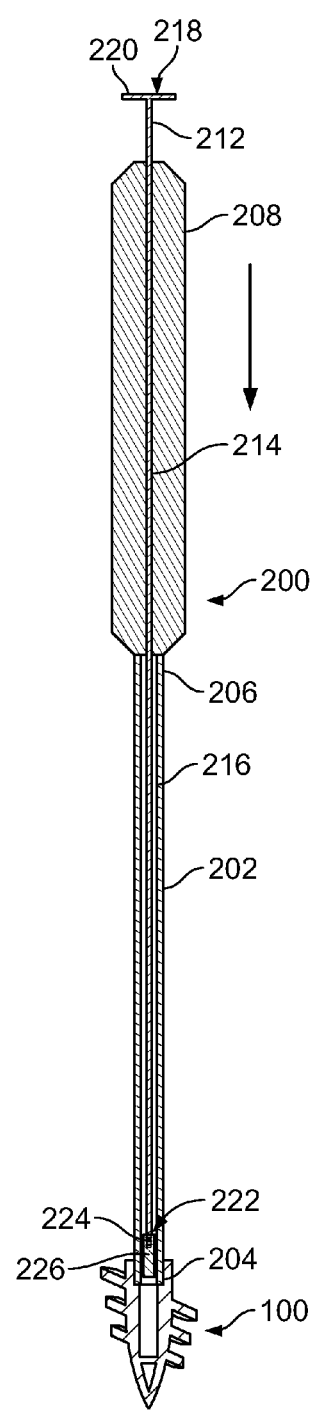
FIG. 5 is a side view of an exemplary suture anchor and driver including a retracted locking pin according to the present disclosure.

Turning now to FIGS. 4 and 5, the suture anchor 100 is provided with an exemplary driver 200. The driver 200 generally includes an elongated tubular or hollow shaft 202 which defines a distal end 204 and a proximal end 206. The distal end 204 of the shaft 202 can be configured and dimensioned to be inserted into and interlocked with the first cavity 112 of the suture anchor 100. For example, the distal end 204 of the shaft 202 can be configured as a hexagon which can enter into and interlock relative to the hexagonal configuration of the first cavity 112 of the suture anchor 100. Thus, rotation of the driver 200 can impart a torque on the suture anchor 100 for driving the suture anchor 100 into tissue and/or bone.

The proximal end 206 of the shaft 202 can be connected to a driver handle 208. Although illustrated as defining a smooth outer surface, in some embodiments, the driver handle 208 can include ridges and/or a friction-imparting surface to prevent slippage of a user's hand during gripping or twisting of the driver handle 208. The driver handle 208 can include a post 210 extending therefrom around which the suture 116 can be wrapped. In some embodiments, the suture 116 can be passed around the internal post 120 of the suture anchor 100, passed out of the internal cavity 110 and wrapped around the post 210 of the driver handle 208 to lock the suture anchor 100 relative to the driver 200 to prevent undesired removal of the distal end 204 of the shaft 202 from the first cavity 112 of the suture anchor 100.

The driver 200 can include an internal locking pin driver 212. The internal locking pin driver 212 can be configured as an elongated rod passing through an aperture 214 formed in the driver handle 208 and through an internal cavity 216 formed in the shaft 202. A proximal end 218 of the locking pin driver 212 can include a cap 220 or handle and a distal end 222 of the locking pin driver 212 can include a locking means 224, e.g., threading, for interlocking relative to an internal locking pin 226. For example, the locking pin 226 can be passed into the internal cavity 216 of the shaft 202 and the locking pin driver 212 can be interlocked relative to the locking pin 226 by threading the locking means 224 into a complementary threaded cavity at the proximal end of the locking pin 226. Thus, axial translation of the locking pin driver 212 can simultaneously axially translate or deploy the locking pin 226 in and out of the distal end 204 of the shaft 202.

As can be seen from FIGS. 4 and 5, the suture 116 can be slidably preloaded or passed around the internal post 120 and out of the suture anchor 100. To interlock the driver 200 and the suture anchor 100, the distal end 204 of the shaft 202 can be inserted into the first cavity 112, i.e., the driver/anchor interface, until the distal end 204 abuts the edge 118 of the suture anchor 100. In particular, the walls of the internal cavity 216 of the shaft 202 can be substantially aligned with the internal walls of the second cavity 114 of the suture anchor 100. The sutures 116 can be wrapped around the post 210 to secure the driver 200 relative to the suture anchor 100. The anchor sutures 116 wrapped around the post 210 can provide longitudinal tension along the handle 208 and/or driver 200, further locking and holding the suture anchor 100 on the distal end 204 or tip of the driver 100 at the driver/anchor interface.

In sliding suture 116 embodiments, the driver 200 can then be axially rotated to drive the suture anchor 100 into the tissue and/or bone, the suture 116 can be unwrapped from the post 210 of the driver handle 208, and the driver 200 can be disengaged from the suture anchor 100. The suture 116 can thereby remain in a sliding engagement with the suture anchor 100. It should be understood that in sliding suture 116 embodiments, inclusion of the locking pin 226 within the shaft 202 of the driver 200 may not be necessary. However, the locking pin 226 can be implemented within the driver 200 even in sliding suture 116 applications to allow a user to decide during application of the suture anchor 100 whether a sliding or a non-sliding suture 116 application is desired.

Figure 6:
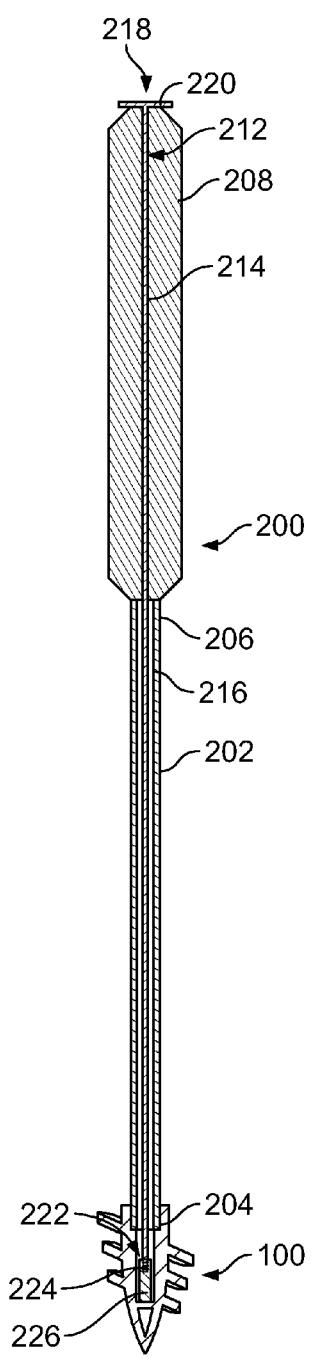
FIG. 6 is a side view of an exemplary suture anchor and driver including an inserted locking pin according to the present disclosure.

In non-sliding suture 116 embodiments, after the driver 200 has been implemented for driving the suture anchor 100 into the tissue and/or bone, the locking pin driver 212 can be depressed against the handle 208 such that the cap 220 abuts the top of the handle 208 (see, e.g., FIG. 6). It should be understood that the suture anchor 100 can be driven into tissue and/or bone with the driver 200 without advancing the internal locking pin 226. When advancement of the locking pin 226 is desired, the locking pin driver 212 can be depressed to advance the locking pin driver 212 and the internal locking pin 226 from the shaft 202 and into the second cavity 114 of the suture anchor 100. In some embodiments, advancement of the locking pin 226 can be performed with, e.g., a screw design, mechanical or automatic actuation of the locking pin driver 212, and the like (not shown). As will be discussed in greater detail below, the locking pin 226 can be configured and dimensioned to lock the suture 116 against the internal walls of the second cavity 114 such that the suture 116 cannot be pulled in or out of the suture anchor 100. The locking pin driver 212 can then be disengaged from the locking pin 226 by, e.g., unscrewing the locking means 224 from the locking pin 226, the sutures 116 can be unwrapped from the post 210, and the locking pin driver 212 and the driver 200 can be disengaged from the suture anchor 100. Thus, non-sliding suture 116 applications can be used with the exemplary suture anchor 100.

With reference to FIG. 7, a side, cross-sectional detailed view of an interlocked driver 200 and suture anchor 100 is provided, for example, prior to deployment into tissue and/or bone. In particular, FIG. 7 shows a driver 200 with a locking pin 226 retracted into the internal cavity 216 of the shaft 202 and away from the suture anchor 100. In some embodiments, the preloaded suture 116 can pass around the internal post 120 of the suture anchor 100 and out of the suture anchor 100 through openings (not shown) in the sides of the shaft 202. In some embodiments, the preloaded suture 116 can pass around the internal post 120 of the suture anchor 100, around the distal end 204 of the shaft 202, and out of the suture anchor 100. The locking means 224 between the locking pin driver 212 and the locking pin 226 can also be seen in FIG. 7. In some embodiments, the locking means 224 can include a complementary mini-fine thread interface between the locking pin driver 212 and the locking pin 226.

With reference to FIG. 8, the suture anchor 100 is shown after being driven into tissue and/or bone 300 for a sliding suture 116 application. In particular, the suture anchor 100 has been driven into the tissue and/or bone 300 with the driver 200, the driver 200 has been disengaged from the suture anchor 100 without advancement of the locking pin 226 into the second cavity 214 of the suture anchor 100, and the suture 116 has been unwrapped from the post 210 of the handle 208. Thus, the locking pin 226 remains within the body or internal cavity 216 of the shaft 202 and the suture 116 can freely slide around the internal post 120 of the suture anchor 100.

Figure 9:
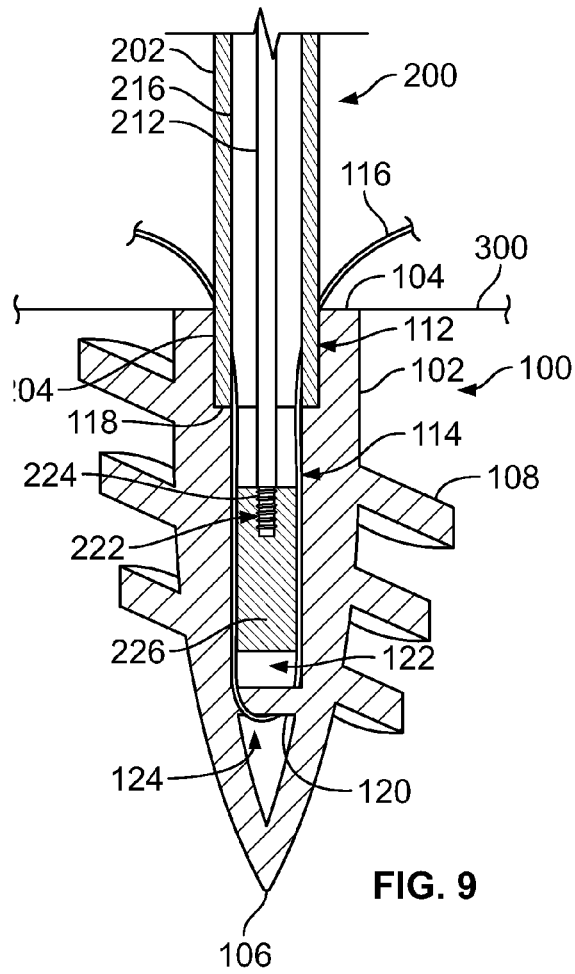
FIG. 9 is a side, cross-sectional view of an exemplary suture anchor and driver including an inserted locking pin according to the present disclosure.
Figure 10:
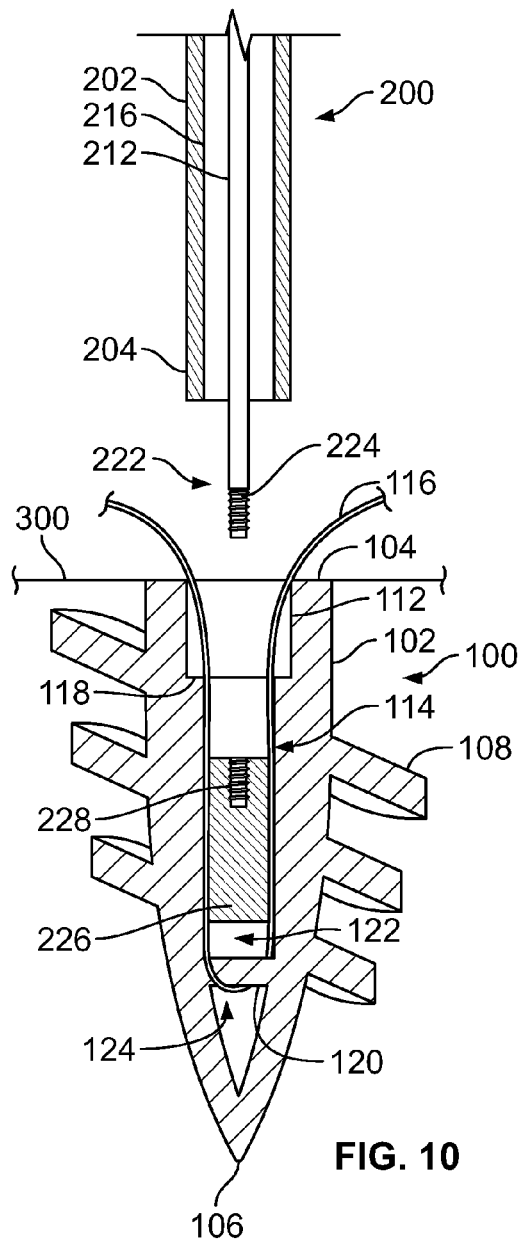
FIG. 10 is a side, cross-sectional view of an exemplary suture anchor and driver including an inserted locking pin according to the present disclosure.

FIGS. 9 and 10 illustrate the implementation of the suture anchor 100 and the driver 200 for non-sliding applications. In particular, once the suture anchor 100 has been driven into the tissue and/or bone 300, the locking pin driver 212 can be depressed against the handle 208 to advance the locking pin 226 into the second cavity 114 of the suture anchor 100. Advancement of the locking pin 226 into the second cavity 114 can push the sutures 116 against the inner walls of the second cavity 114 to provide, e.g., an interference fit, a frictional lock fit, and the like, which prevents the sutures 116 from sliding around the internal post 120. Thus, the configuration and dimensions of the locking pin 226 and the second cavity 114 can be determined such that one or more sutures 116 can fit between the locking pin 226 and the second cavity 114 walls, while an interference fit and/or frictional fit is created due to the pressure of the locking pin 226 against the sutures 116 and the second cavity 114 walls. In some embodiments, rather than or in addition to the friction or interference fit, the outer surfaces of the locking pin 226 can include threads and the inner surfaces of the second cavity 114 can include threading complementary to the threads on the locking pin 226. Thus, the locking pin 226 can be threaded into the second cavity 114 of the suture anchor 100 to press the sutures 116 against the side walls of the second cavity 114 and/or against the internal post 120.

Although illustrated in FIGS. 9 and 10 as being positioned in a space between the internal post 120 and the first cavity 112, i.e., spaced from the internal post 120, in some embodiments, the locking pin 226 can be advanced into the second cavity 114 until the locking pin 226 abuts the internal post 120. In some embodiments, the locking pin 226 can be dimensioned to extend from the internal post 120 to the edge 118 of the suture anchor 100, i.e., the full length of the untapered section of the second cavity 114. In some embodiments, the locking pin 226 dimension can be varied so long as the locking pin 226 provides sufficient surface area for maintaining the sutures 116 within the second cavity 114 of the suture anchor 100. The sutures 116 can then be unwrapped from the post 210 of the handle 208, the locking means 224 of the locking pin driver 212 can be disengaged, e.g., unscrewed, from the complementary locking means 228 in the locking pin 226 (see, e.g., FIG. 10), and the shaft 202 can be withdrawn from the first cavity 112 of the suture anchor 100.

Figure 11:
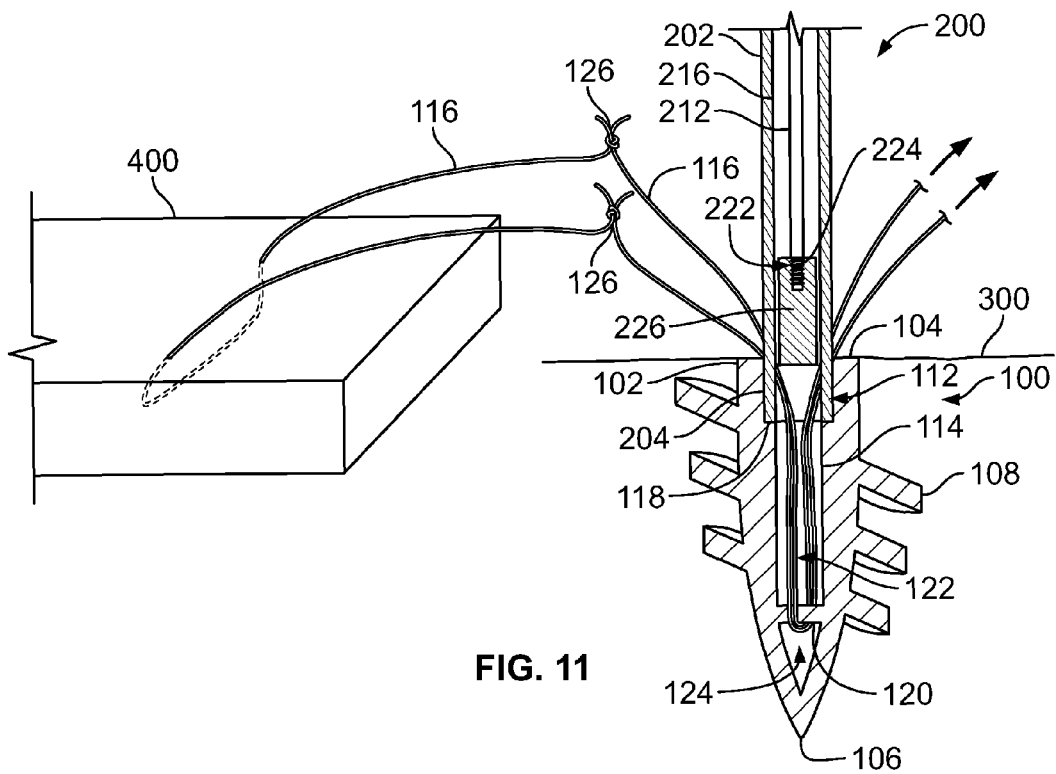
FIG. 11 is a side view of an exemplary suture anchor securing a suture in tissue according to the present disclosure.
Figure 12:
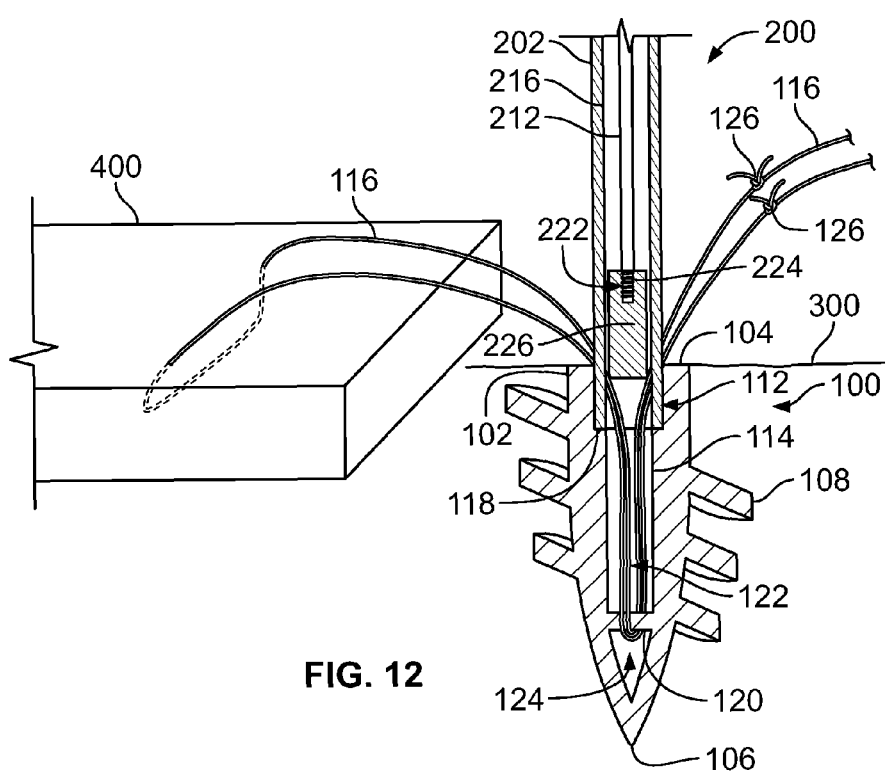
FIG. 12 is a side view of an exemplary suture anchor securing a suture in tissue according to the present disclosure.

Turning now to FIGS. 11-15, knotless techniques or applications of securing sutures 116 with the suture anchor 100 are provided. For example, the knotless techniques can be used to secure sutures 116 which have already been passed through soft tissue 400. Therefore, in some embodiments, the suture anchors 100 can be used as suture 116 shuttles. One suture 116 or suture limb can be passed through the soft tissue 400, e.g., tendon, and can be extended out of the soft tissue 400. A second suture 116 or suture limb can be slidably preloaded into the suture anchor 100 prior to driving the suture anchor into the tissue and/or bone 300. The second suture 116 protruding out of the suture anchor 100 can be secured to the first suture 116 extending out of the soft tissue 400 by, e.g., tying knots 126 between the two sets of sutures 116. By pulling on the suture 116 limbs of the anchor suture 116 as illustrated by the arrows of FIG. 11, the soft tissue 400 sutures 116 can be shuttled around the suture anchor 100 bottom portion 124, i.e., eyelet, and the internal post 120 and through the anchor body 102 of the suture anchor 100. The sutures 116 passing through the soft tissue 400 can thereby be tightened through the suture anchor 100.

Figure 13:
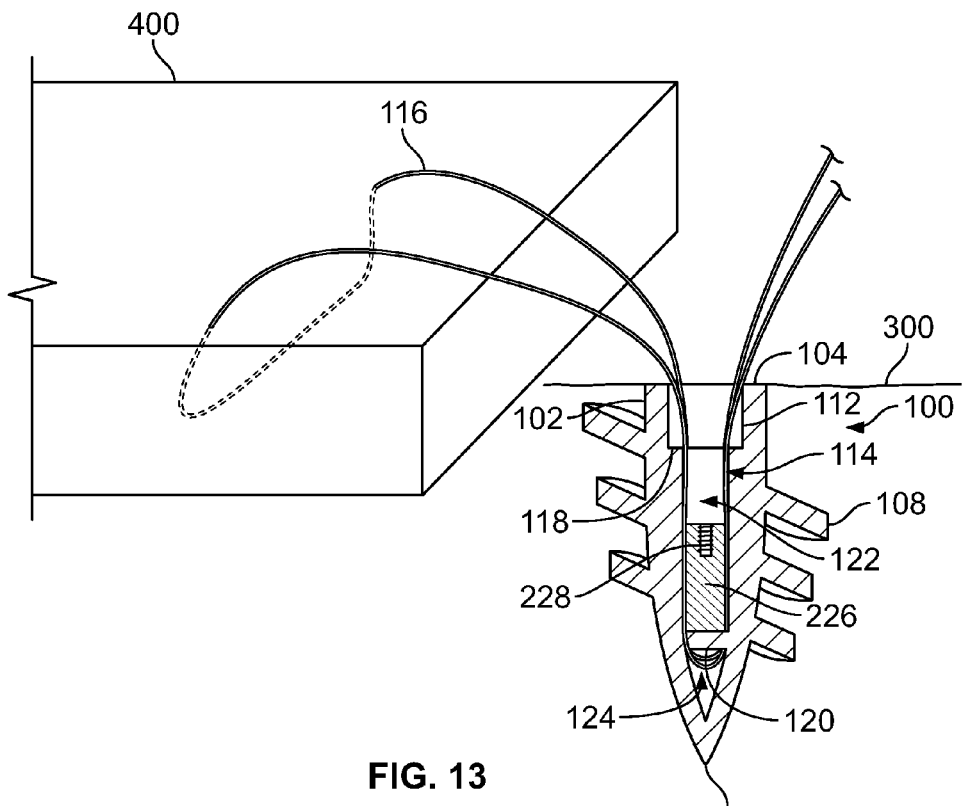
FIG. 13 is a side view of an exemplary suture anchor securing a suture in tissue according to the present disclosure.

When the appropriate tendon or soft tissue 400 reduction and/or suture 116 tension has been achieved, the user can decide whether the locking pin 226 should be advanced into the suture anchor 100. FIG. 13 illustrates an implementation of the knotless technique with an advanced locking pin 226. In particular, the sutures 116 have been pulled through the suture anchor 100 to tighten the sutures 116 relative to the soft tissue 400 and/or to reduce the soft tissue 400 towards the suture anchor 100 and the locking pin 226 has been advanced into the second cavity 114 of the suture anchor 100 to lock the sutures 116 against the inner walls of the second cavity 114. The sutures 116 can thereby be locked in place in a knotless manner. It should be understood that once the locking pin 226 has been advanced into the suture anchor 100, the driver 200 can be disengaged from the suture anchor 100 as discussed above.

Figure 14:
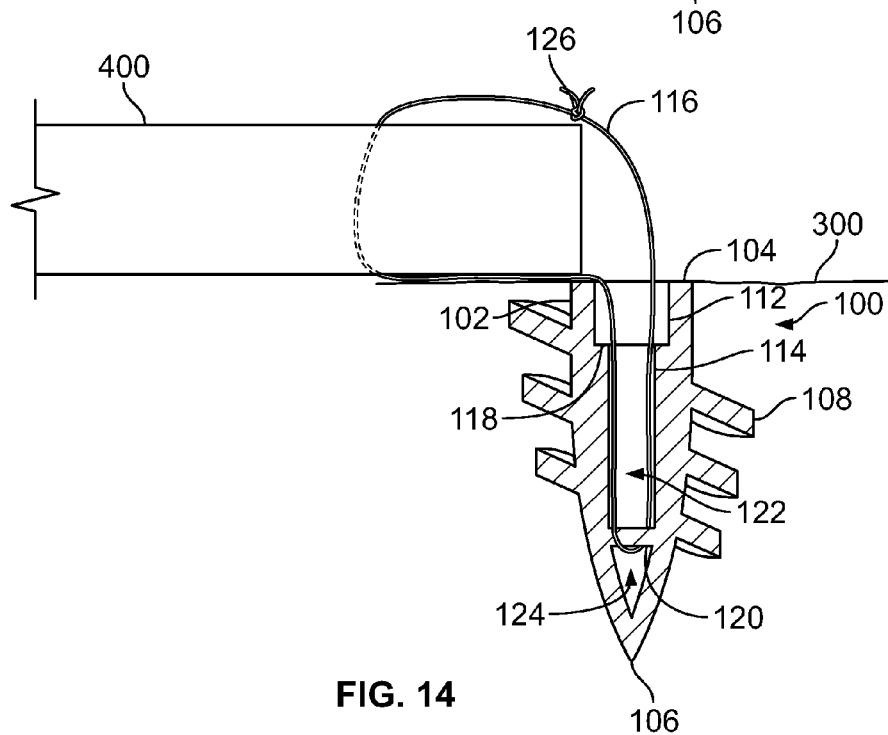
FIG. 14 is a side view of an exemplary suture anchor securing a suture in tissue according to the present disclosure.

FIG. 14 illustrates an implementation of a single-row, sliding technique without advancing the locking pin 226 into the suture anchor 100. In particular, the suture 116 has been pulled through the suture anchor 100 to tighten the suture 116 relative to the soft tissue 400 and/or to reduce the soft tissue 400 towards the suture anchor 100 and a knot 126 has been tied to connect the two sides of the suture 116 relative to each other. The knot 126 can be tied to maintain the desired tension of the sutures 116 relative to the soft tissue 400. In addition, the suture 116 can freely slide relative to the suture anchor 100.

In some embodiments, as shown in the single-row, non-sliding technique of FIG. 15, the knot 126 can be implemented to secure the two sides of the suture 116 relative to each other in conjunction with the advanced locking pin 226. Thus, for example, only one portion of the suture 116 can be passed around the internal post 120 of the suture anchor 100 and the locking pin 226 can be advanced into the second cavity 114 to secure the suture 116 against the inner walls of the second cavity 114 with, e.g., a friction fit, and interference fit, and the like. The driver 200 can be disengaged from the suture anchor 100 and the suture 116 protruding from the suture anchor 100 can be tied with a knot 126 to the suture 116 protruding from the soft tissue 400 for a non-sliding suture 116 application.

In addition to the single-row techniques described above, the one or more suture anchors 100 can be used to perform double-row fixation of soft tissue to bone. FIG. 16 shows a knotted, double-row technique using a medial suture anchor 100a and a lateral suture anchor 100b. In particular, the medial suture anchor 100a can be slidably preloaded with a suture 116 around the internal post 120 and the medial suture anchor 100a can be driven into the tissue and/or bone 300 underlying the soft tissue 400. The sutures 116 of the medial suture anchor 100a can be used in a sliding manner, i.e., a locking pin 226 is not used to secure the suture 116 relative to the medial suture anchor 100a, and the sutures 116 can be further passed through the medial aspect of the soft tissue 400, e.g., a tendon. A knot 126 can then be tied in the suture 116 on the superior surface of the soft tissue 400. Further, the suture 116 ends can be shuttled through the lateral suture anchor 100b driven into the adjacent tissue and/or bone 300 and an internal locking pin 226 can be used to secure the suture 116 within the lateral suture anchor 100b. Thus, the desired tension in the suture 116 can be maintained.

FIG. 17 shows a knotless, double-row technique using a medial suture anchor 100a and a lateral suture anchor 100b. In particular, the medial suture anchor 100a can be slidably preloaded with a suture 116 around the internal post 120 and the medial suture anchor 100a can be driven into the tissue and/or bone 300 underlying the soft tissue 400. The sutures 116 of the medial suture anchor 100a can be used in a non-sliding manner by advancing a locking pin 226 into the second cavity 114 of the medial suture anchor 100a to secure the sutures 116 therein. The sutures 116 can then be passed through the medial aspect of the soft tissue 400, e.g., a tendon. Due to the non-sliding nature of the sutures 116 relative to the medial suture anchor 100a, a knot does not need to be tied on the superior surface of the soft tissue 400. In some embodiments, a user can tie a knot 126 substantially similar to the knot 126 shown in FIG. 16 on the superior surface of the soft tissue 400 for additional fixation of the suture 116. The suture 116 ends can then be shuttled through the lateral suture anchor 100b driven into the adjacent tissue and/or bone 300 and an internal locking pin 226 can be used to secure the suture 116 within the lateral suture anchor 100b. In some embodiments, the suture 116 ends can be preloaded into the lateral suture anchor 100b prior to driving the lateral suture anchor 100b into the tissue and/or bone 300. Thus, the desired tension in the suture 116 can be maintained.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A suture anchor, comprising:
a suture anchor body with a distal end and a proximal end, and that includes a securing structure for securing the suture anchor in tissue or bone,
wherein the suture anchor body includes an internal cavity that extends from the distal end to the proximal end, configured and dimensioned to receive therein a suture and a locking pin, and comprising a single opening that is located at the proximal end and an internal post that forms an eyelet in the internal cavity.

2. The suture anchor according to claim 1, wherein the suture anchor body is adapted for sliding, non-sliding and knotless suturing techniques.

3. The suture anchor according to claim 1, wherein the securing structure is at least one of threads, an interference fit surface, and a retractable harpoon.

4. The suture anchor according to claim 1, wherein the suture anchor body comprises an additional internal cavity located adjacent to the internal cavity configured and dimensioned to interlock with a driver for driving the suture anchor into the tissue or bone.

5. The suture anchor according to claim 1, wherein the eyelet is configured and dimensioned to receive the suture therethrough.

6. The suture anchor according to claim 1, wherein the suture anchor body is fabricated from a group consisting of a metal, a bioabsorbable material, a biocomposite material, and a polyether ether ketone.

* * * * *